(12) United States Patent
Thompson et al.

(10) Patent No.: US 11,554,344 B2
(45) Date of Patent: *Jan. 17, 2023

(54) COPPER (II)-EXCHANGED SMALL-PORE ZEOLITES FOR IMPROVED ETHYLENE SEPARATION OVER ETHANE

(71) Applicant: CHEVRON U.S.A. INC., San Ramon, CA (US)

(72) Inventors: Joshua A. Thompson, Martinez, CA (US); Dan Xie, El Cerrito, CA (US); Joel Edward Schmidt, Oakland, CA (US); Stacey Ian Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/524,892

(22) Filed: Nov. 12, 2021

(65) Prior Publication Data

US 2022/0143544 A1 May 12, 2022

Related U.S. Application Data

(60) Provisional application No. 63/112,730, filed on Nov. 12, 2020.

(51) Int. Cl.
*B01D 53/047* (2006.01)
*C07C 7/13* (2006.01)
(Continued)

(52) U.S. Cl.
CPC ............ *B01D 53/047* (2013.01); *B01J 20/18* (2013.01); *C07C 7/005* (2013.01); *C07C 7/13* (2013.01);
(Continued)

(58) Field of Classification Search
CPC ............ B01D 53/047; B01D 2253/108; B01D 2253/1085; B01D 2256/24; B01D 2257/102; B01D 2257/108; B01D 2257/7022; B01D 2259/40013; B01D 2259/40035; B01D 2259/40052;
(Continued)

(56) References Cited

U.S. PATENT DOCUMENTS

| 9,409,786 B2 * | 8/2016 | Xie | B01J 29/50 |
| 2008/0159936 A1 * | 7/2008 | Zones | B01D 53/04 |
| | | | 423/212 |

(Continued)

FOREIGN PATENT DOCUMENTS

WO 0212152 A1 2/2002

OTHER PUBLICATIONS

PCT International Search Report and Written Opinion re International Application PCT/IB2021/060483 dated Feb. 22, 2022 containing 14 pages.

(Continued)

*Primary Examiner* — Youngsul Jeong
*Assistant Examiner* — Jason Y Chong
(74) *Attorney, Agent, or Firm* — Howard Owens

(57) ABSTRACT

The present invention and embodiments thereof provide a process to separate ethylene products from impurities such as nitrogen, hydrogen, ethane, propane and isobutane without the need for distillation processes.

12 Claims, 8 Drawing Sheets

(51) Int. Cl.
*B01J 20/18* (2006.01)
*C07C 7/00* (2006.01)

(52) U.S. Cl.
CPC .... *B01D 2253/108* (2013.01); *B01D 2256/24* (2013.01); *B01D 2257/102* (2013.01); *B01D 2257/108* (2013.01); *B01D 2257/7022* (2013.01); *B01D 2259/402* (2013.01); *B01D 2259/40013* (2013.01); *B01D 2259/40035* (2013.01); *B01D 2259/40052* (2013.01); *B01D 2259/40064* (2013.01)

(58) Field of Classification Search
CPC .... B01D 2259/40064; B01D 2259/402; B01D 2259/404; B01J 20/18; C07C 7/005; C07C 7/13
See application file for complete search history.

(56) References Cited

U.S. PATENT DOCUMENTS

| | | |
|---|---|---|
| 2014/0072494 A1 | 3/2014 | Zones et al. |
| 2016/0002060 A1 | 1/2016 | Xie et al. |
| 2017/0072359 A1* | 3/2017 | Thompson ............... B01J 20/18 |
| 2018/0257019 A1* | 9/2018 | Thompson ............... C10L 3/102 |

OTHER PUBLICATIONS

Ramani Balan: "Pressure swing adsorption cycle design for ethylene/ethane separation process", Jan. 1, 2015 (Jan. 1, 2015), XP055847675, Retrieved from the Internet: URL:http://resolver.tudelft.nl/uuid:a1affc57-5988-493f-b5ce-946bf7e50cd6 [retrieved on Oct. 5, 2021] p. 17-p. 20.

Abdi Hamed et al.: "Adsorption properties of ion-exchanged SSZ-13 zeolite for ethylene/ethane separation", Fluid Phase Equilibria, vol. 546, Oct. 1, 2021 (Oct. 1, 2021), p. 113171, XP55887065, Amsterdam, NL ISSN: 0378-3812, DOI: 10.1016/j.fluid.2021. 113171 Retrieved from the Internet: URL:https://www.sciencedirect.com/science/article/pii/S0378381221002338/pdfft?md5=ecald31656c0d38422371a93a31e7333&pid=1-s2.0-S0378381221002338-main.pdf> the whole document.

* cited by examiner

COPPER (II)-EXCHANGED SMALL-PORE ZEOLITES FOR IMPROVED ETHYLENE SEPARATION OVER ETHANE

FIELD

The present invention and embodiments thereof provide a process to separate ethylene products from impurities such as nitrogen, hydrogen, ethane, propane and isobutane without the need for distillation processes.

BACKGROUND

Ethylene-ethane separations for current commercial applications require the use of very large distillation towers and energy requirements in order to separate ethylene to a polymer-grade level. In the polyethylene plant there are stranded gas streams containing significant ethylene content, ranging from 50 to greater than 90 mol %. Due to the intensive process currently used, these gas streams cannot be recycled or recovered at smaller scales. In prior art, some membrane technologies have been developed that have moderate ethylene membrane selectivity, typically less than 10.

Pressure-swing adsorption (PSA) technology is an alternative technology for recovering stranded ethylene in a polyethylene plant that uses a solid adsorbent material to remove impurities that include ethane, hydrogen, nitrogen and methane gas. The adsorbent selection can function as either an equilibrium-based or kinetic-based separation. In principle, all adsorption processes utilize at least two steps: adsorption or uptake of the target molecule in the adsorbent; and desorption or removal of the same target molecule from the adsorbent. This may be achieved by changes in concentration, pressure, or temperature. In the case of PSA and vacuum-swing adsorption (VSA), pressure changes are used to regenerate the adsorbent. PSA does not require a dehydration step necessarily prior to separation of target components. PSA technology is able to treat stranded ethylene gas to recover ethylene up to a target purity of at least 98 mol % without the use of distillation or other thermally-driven separation processes.

It would be desirable to have a PSA or VSA process utilizing an adsorbent material which would require lower vacuum power consumption or elimination of vacuum entirely while allowing for improved recovery of ethylene product. Such a process would enable deployment and competitive use of PSA units to recover stranded ethylene gases.

SUMMARY

In one embodiment a method is provided for removing impurities found in a polyethylene plant from a stranded ethylene gas stream. These impurities include methane, nitrogen, hydrogen and ethane, but may also include propane and isobutane.

A further embodiment is a method to separate ethylene products from impurities such as nitrogen, hydrogen, ethane, propane and isobutane without the need for distillation processes.

A further embodiment of the method includes alternating input of the feed gas stream between at least two beds of adsorbent particles comprising a zeolite with either CHA or ERI framework such that the feed gas stream contacts one of the at least two beds at a given time in an adsorption step and a tail gas stream is simultaneously vented from another of the at least two beds in a desorption step. A slip stream of the tail gas may be compressed and recycled as a rinse step for a bed after the adsorption step. The contact occurs at a feed pressure of from about 50 to about 500 psia for a sufficient period of time to preferentially adsorb ethylene over other impurities in the gas stream. A tail gas stream is produced containing no greater than 2 mol % of impurities and at least 98 mol % purity of ethylene. The feed gas stream is input at a feed end of each bed. The tail gas stream is removed by depressurization of the bed and desorption of ethylene adsorbed on the zeolite adsorbent with either CHA or ERI framework. The tail gas is produced from the feed end of each bed during the desorption step. A slip-stream of the tail gas may be compressed and used as a rinse stream for a bed after the adsorption step. The rinse stream is also input at the feed each of each bed, and serves to further push impurities toward the outlet of the bed. The impurity-rich stream produced from the bed outlet during the adsorption and rinse steps have less than the feed composition of ethylene and may be utilized as a fuel gas or other gas stream within the polyethylene plant.

DETAILED DESCRIPTION

Figure 1:
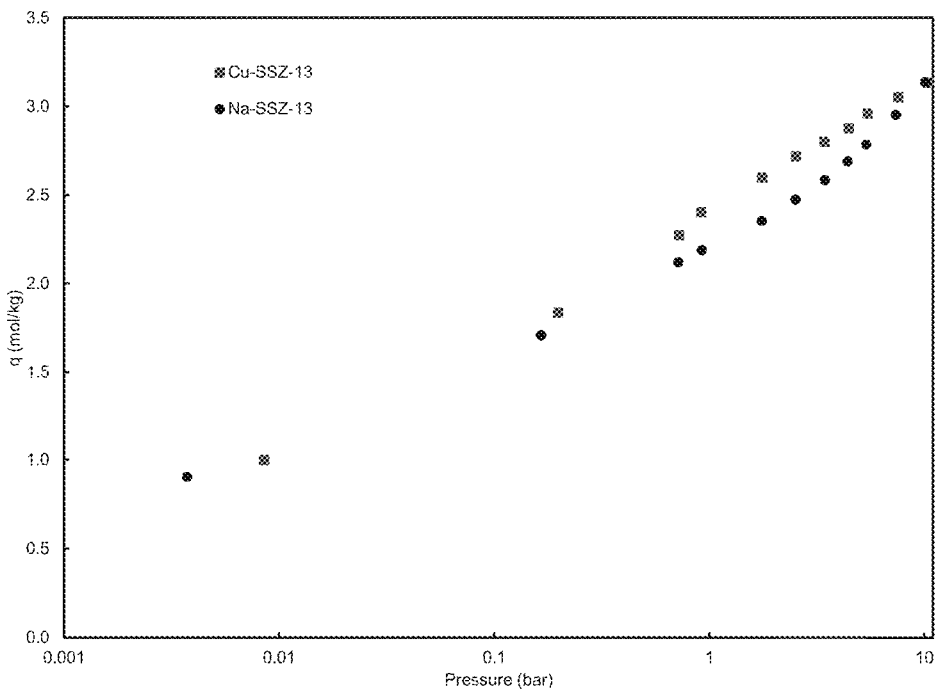
FIG. 1 is a plot of gas adsorption isotherms of C2H4 at 30 degrees C. for Cu-SSZ-13 and Na-SSZ-13.

The methods of the present disclosure use zeolite particles comprised of either a CHA or ERI framework as an adsorbent material in a cyclic adsorption process for upgrading ethylene product from at least 50 mol % to at least 98 mol %. The other components in the stream can be ethane and larger hydrocarbons as well as N2, CH4 and H2.

In one embodiment, methods and processes of the present disclosure use alternative adsorbent particles that comprise a zeolite with either a CHA or ERI framework to remove the contaminants from a feed gas stream. Zeolites are crystalline solid structures made of silicon, aluminum and oxygen that form a framework with cavities and channels inside where cations, water and/or small molecules may reside. Zeolites are crystalline aluminosilicates with open 3D framework structures built of SiO4 and AlO4 tetrahedra linked to each other by sharing all the oxygen atoms to form regular intra-crystalline cavities and channels of molecular dimensions. A defining feature of zeolites is that their frameworks are made up of 4-coordinated atoms forming tetrahedra. These tetrahedra are linked together by their corners and make a rich variety of structures. The framework structure may contain linked cages, cavities or channels, which are big enough to allow small molecules to enter. The system of large voids explains the consistent low specific density of these compounds. The aluminosilicate framework is negatively charged and can attract positive cations that reside in the cages as a framework ion and can compensate for the negative charge of the framework.

The zeolites disclosed here are examples of synthetic zeolites with either a CHA or ERI framework type. Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types," Sixth Revised Edition, Elsevier (2007).

CHA framework type molecular sieves, or zeolites, are characterized by three-dimensional 8-membered-ring pore/channel systems and an interconnecting cage. Zeolite SSZ-13 is a small pore zeolite containing channels less than 4.2 angstrom in diameter and cages less than 8.0 angstrom in length. The zeolite composition is made up of both silica and alumina and, therefore, has extra-framework cations that balance the negative charge of the framework.

ERI framework type molecular sieves, or zeolites, are characterized by three-dimensional 8-membered-ring pore/channel systems and an interconnecting cage. Zeolite SSZ-98 is a small pore zeolite containing channels less than 3.3 angstrom in diameter and cages less than 7.7 angstrom in length. The zeolite composition is made up of both silica and alumina and, therefore, has extra-framework cations that balance the negative charge of the framework.

In one embodiment, the zeolite SSZ-13 with a CHA framework has a Si:Al ratio of 5 or greater, such as from 5 to 100. In one embodiment, the Si:Al mole ratio can be from greater than 5 to 80, such as from 10 to 50, or from 10 to 35.

In one embodiment, the zeolite SSZ-98 with a ERI framework has a Si:Al ratio of 5 or greater, such as from 5 to 100. In one embodiment, the Si:Al mole ratio can be from greater than 5 to 80, such as from 10 to 50, or from 10 to 35.

In one embodiment the zeolite SSZ-13 is formed into the adsorbent particles by pressing into pellets. In one embodiment, the adsorbent particles can be a component in a membrane that is used for removing the impurities from the feed gas stream that is ethylene-rich. Some examples of mixed-matrix membranes with dispersed adsorbent particles are described in U.S. Pat. No. 6,508,860.

In one embodiment, the zeolite SSZ-13 can be formulated into the adsorbent particles using a combination with other materials, such as binders and/or matrix materials, which provide additional hardness or adsorbent activity to the adsorbent particles. When used, the relative proportions of the zeolite SSZ-13 and other materials may vary widely with the zeolite or molecular sieve content ranging from 1 to 90 wt %, or from 2 to 80 wt % of the adsorbent particles.

In one embodiment the zeolite SSZ-98 is formed into the adsorbent particles by pressing into pellets. In one embodiment, the adsorbent particles can be a component in a membrane that is used for removing the impurities from the feed gas stream that is ethylene-rich. Some examples of mixed-matrix membranes with dispersed adsorbent particles are described in U.S. Pat. No. 6,508,860.

In one embodiment, the zeolite SSZ-98 can be formulated into the adsorbent particles using a combination with other materials, such as binders and/or matrix materials, which provide additional hardness or adsorbent activity to the adsorbent particles. When used, the relative proportions of the zeolite SSZ-98 and other materials may vary widely with the zeolite or molecular sieve content ranging from 1 to 90 wt %, or from 2 to 80 wt % of the adsorbent particles.

In one embodiment, the adsorbent particles are made from a homogeneous mixture and are not coated particles or made from layers of different materials. An example of how these adsorbent particles can be made is when the adsorbent particles are pressed into pellets from a powder. In one embodiment, the zeolite is mixed with a catalyst support and the zeolite and the catalyst support are ground together into a powder that is a homogeneous mixture. In one embodiment the catalyst support is alumina, such as a pseudo-Boehmite alumina powder. The catalyst support can be inert or can participate in the adsorption performed by the adsorbent particles. Typical catalyst supports include various kinds of carbon, alumina, and silica. In one embodiment, the catalyst support comprises an amorphous silica aluminate. In one embodiment, the catalyst support comprises an amorphous silica aluminate and a second support material.

Examples of the catalyst support or the second support material (when used), can include kieselguhr, alumina, silica, and silica-alumina. Other examples include alumina-boric, silica-alumina-magnesia, silica-alumina-titania and materials obtained by adding other zeolites and other complex oxides thereto. In one embodiment, the catalyst support is porous, and comprises a natural clay or a synthetic oxide. The catalyst support can be selected to provide adequate mechanical strength and chemical stability at the contacting conditions under which the adsorbent particles are employed.

In one embodiment, the catalyst support or the second support material comprises a pseudo-boehmite alumina. Examples of pseudo-boehmite alumina are CATAPAL® high purity aluminas. CATAPAL® is a registered trademark of Sasol Limited. The pressed pellets can be broken and sieved to obtain the desired mesh size. In one embodiment, the powder X-ray diffraction (XRD) pattern of the pressed pellets is the same as the original XRD pattern of the zeolite powder prior to it having been pressed into a pellet.

In one embodiment, the zeolite SSZ-98 has a cation as a framework ion. The cation can be selected from the group consisting of a sodium, a calcium, a potassium, a lithium, a magnesium, a barium, a copper, a silver, a platinum, a paladium, a hydrogen and combinations thereof. In one embodiment, the cation is sodium. In one embodiment, the cation is copper. The choice of the cation can change the adsorption performance of the adsorbent particles.

In one embodiment, the zeolite SSZ-13 has a cation as a framework ion. The cation can be selected from the group consisting of a sodium, a calcium, a potassium, a lithium, a magnesium, a barium, a copper, a silver, a platinum, a paladium, a hydrogen and combinations thereof. In one embodiment, the cation is sodium. In one embodiment, the cation is copper. The choice of the cation can change the adsorption performance of the adsorbent particles.

In one embodiment, the method comprises alternating an input of the feed gas stream between at least two beds of the one or more adsorbent particles. In one embodiment, the at least two beds of the one or more adsorbent particles are up to ten beds of the one or more adsorbent particles. The feed gas stream can contact one of the at least two beds at a given time by an adsorption step and a tail gas stream can be simultaneously vented from another of the at least two beds by a desorption step to recover high purity ethylene.

In one embodiment, the desorbed high purity ethylene product stream is compressed to from about 500 to 700 psia and recycled to a polyethylene reactor.

Figure 10:
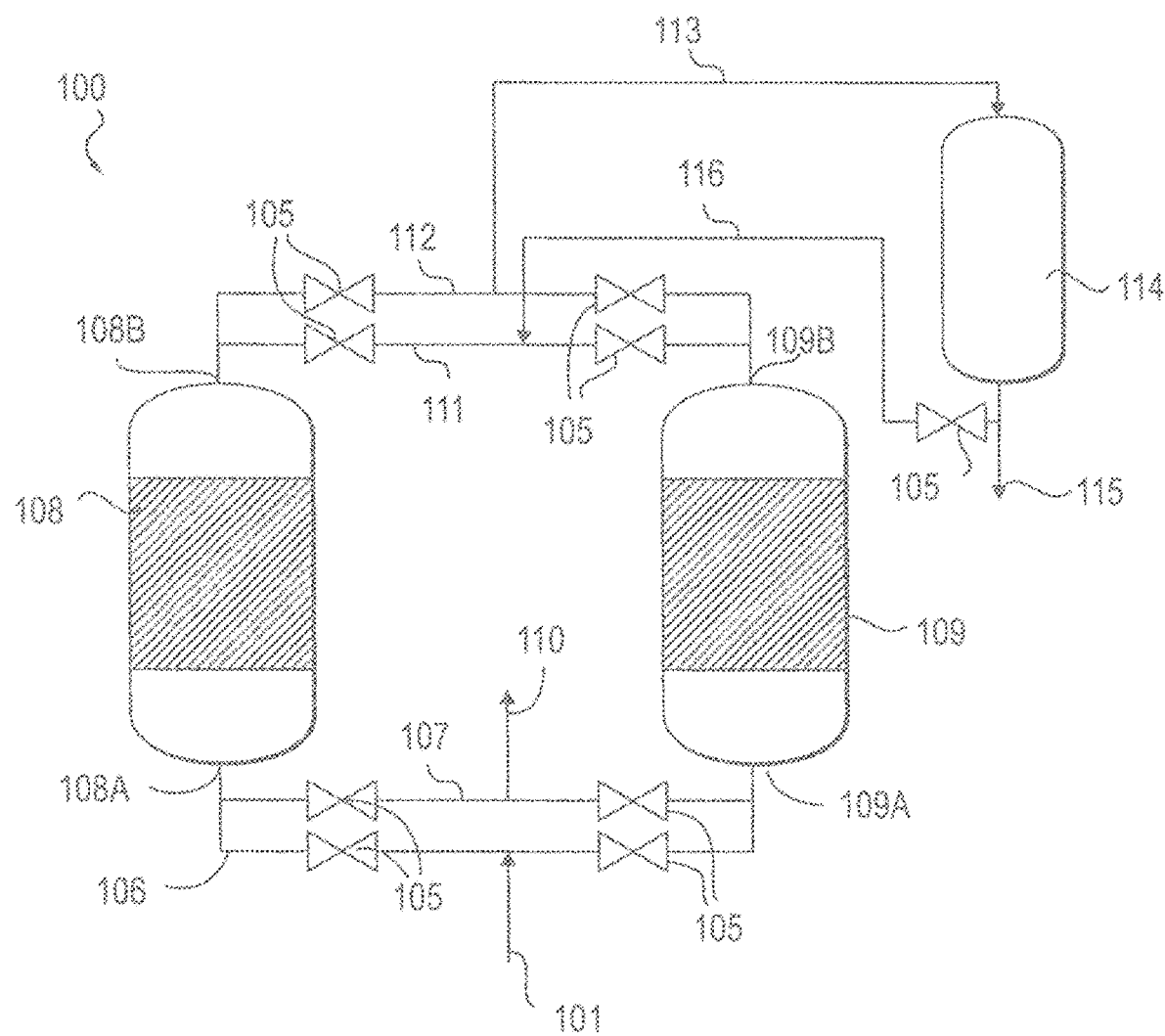
FIG. 10 is an example of pressure-swing adsorption system for recovering ethylene from ethane.

Referring to FIG. 10, here is shown an exemplary two bed PSA system (100) with two beds. In this figure, a feed gas stream (101) is introduced into line (106) having block valves (105) therein. Line (106) connects the first inlet end (108A) to the first adsorption column (108), and also connects the second inlet end (109A) to the second adsorption column (109). A second line (107), is fluidly connected to line (106) and separately connects the first inlet end (108A) to the first adsorption column (108), and also connects the second inlet end (109A) to the second adsorption column (109). Second line (107) has an outlet for tail gas (110). The first adsorption column (108) contains the adsorbent particles described herein, and has a first product end (108B). The second adsorption column (109) also contains the adsorbent particles described herein, and has a second product end (109B). The first product end (108B) and the second product end (109B) are connected by a third line (111) and by a fourth line (112). The third line (111) and the fourth line (112) contain block valves (105). The fourth line (112) is connected with a fifth line (113), which delivers an intermediate product gas stream to a product gas buffer tank (114). The product gas buffer tank (114) allows for controlled purging and re-pressurization steps. The product gas stream (115) can be provided from the product gas buffer tank (114). The product gas buffer tank is controlled by one or more block valves (105) through a sixth line (116) that connects to the third line (111), as shown.

In one embodiment, wherein the method utilizes two beds of the one or more adsorbent particles, the method further comprises:
 a. following the adsorption step in one of the two beds and a simultaneous desorption step in the other of the two beds,
 b. taking a slip stream of the tail gas produced during the desorption step, compressing the slip stream to feed gas pressure, and flowing the compressed slip stream as a rinse stream to the bed after the adsorption step
 c. equalizing a pressure of the two beds through the product end of each of the two beds at the end of the rinse step and the simultaneous desorption step; and
 d. re-pressurizing the bed having just completed the simultaneous desorption step and pressure equalization step by sending the feed gas through the feed end of the bed while closing the outlet of the bed To properly assess and compare adsorbents, simulations were carried out with similar ethylene productivity to compare the process performance of each other. To understand the need of the rinse step of the cycle, each PSA simulation with a different adsorbent was assessed with changing rinse-to-feed (RIF) ratio to determine impact on ethylene purity and recovery. As the RIF ratio increased, there was a sharp drop in the amount of ethylene recovered while drastically increasing the ethylene purity overall. The following adsorbents were studied for their separation potential: Cu-SSZ-13, Cu-SSZ-98, Na-13X, and Zeolite 5A. The first two were chosen to understand how well the separation of ethylene from ethane occurred for novel small-pore zeolites that have been ion-exchanged with copper while the latter two were chosen as benchmarks against any novel adsorbents that may be considered for this separation. The cyclic steady state for each simulation was determined by monitoring the mass and energy balance and stopping once an absolute difference of 1e-05 kmol and 1e-05 MJ was observed between the previous and current cycles. For the blowdown step, a desorption pressure for all simulations was assumed to be 0.1 bar. The feed conditions were at 20 bar and 18.85° C. The feed composition were 60:40 ethylene:ethane gas mixture.

Figure 9:
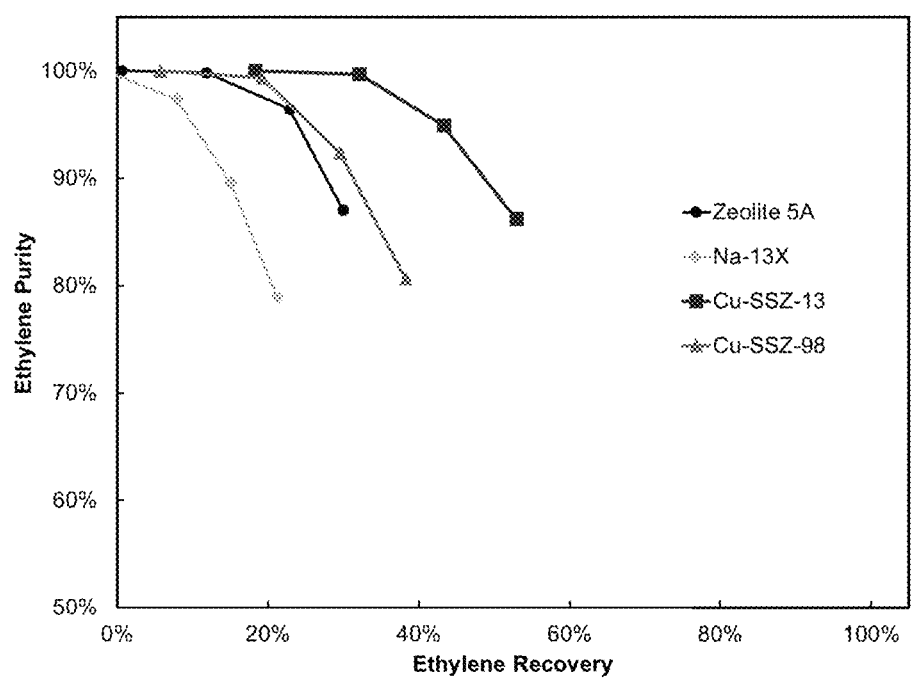
FIG. 9 is a plot of Recovery-purity plot of adsorbents simulated for PSA separation at 20 bar and 18.85° C. Feed gas mixture was 60:40 ethylene:ethane.

The summary of the PSA simulations is shown as a recovery-purity plot for each adsorbent, FIG. 9. Here, the results of the simulation demonstrate the trade-off in achieving high purity ethylene against losing more ethylene to the ethane-enriched tail gas. For all adsorbents, as the ethylene purity increases, especially above 98%, the recovery reduces dramatically. The observed process performance in FIG. 9 correlates with the overall selectivity of each adsorbent. Cu-SSZ-13, while having the highest predicted adsorption selectivity in Example 5, has the overall highest PSA performance shown in FIG. 9. The next best-performing adsorbent is Cu-SSZ-98, which had the next highest adsorption selectivity in Example 5. Both of these small-pore zeolites with copper exchanged in the zeolite exceed the benchmark adsorbents Na-13X and Zeolite 5A, shown in FIG. 9.

EXAMPLES

Example 1: Ion Exchange of Zeolites with Copper

Copper exchanged zeolites were prepared by the following solution. First, copper nitrate was dissolved in deionized water at a concentration of 1.0 g Cu(NO3)2 in 50 mL of water. Powder zeolite sample of 0.5 g was added to the copper solution and heated to 80 degrees C. The solution was stirred at 80 degrees C. for 4 hours. The solution was cooled to room temperature, the salt solution was decanted and then additional salt solution was added. This was repeated two times. The final zeolite powder was rinsed with deionized water at room temperature and then dried at 80 degrees C.

Example 2: Pure Component Equilibrium Adsorption on Copper-Exchanged SSZ-13

Equilibrium gas adsorption experiments for C2H4 and C2H6 were performed on a HPVA 200-4 4-port volumetric system. Samples were first activated at 300° C. to obtain the dry weight and then reactivated in the gas adsorption system. Gases used were C2H4, C2H6, and He (all 99.999%). The zeolites were tested from 0-10 bar for both C2H4 and C2H6. To demonstrate the capability of copper improving the adsorption affinity of ethylene over ethane, zeolites not ion-exchanged with copper were also tested under the same conditions.

Figure 2:
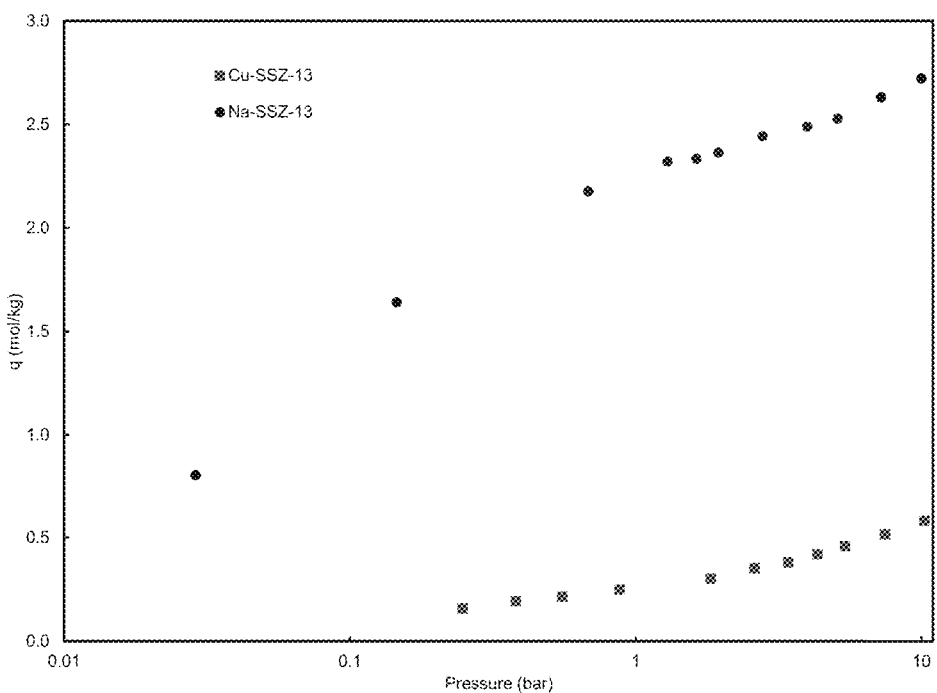
FIG. 2 is a plot of gas adsorption isotherms of C2H6 at 30 degrees C. for Cu-SSZ-13 and Na-SSZ-13.

FIG. 1 shows the equilibrium adsorption results for gas adsorption tests of ethylene for SSZ-13 zeolites samples containing either sodium or copper as the framework cation. FIG. 2 shows equilibrium adsorption results for gas adsorption tests of ethane for the SSZ-13 zeolite samples containing either sodium or copper as the framework cation. While FIG. 1 demonstrates that the presence of copper maintains a high degree of affinity toward ethylene adsorption, FIG. 2 reveals that the presence of the copper in the SSZ-13 zeolite reduces the uptake of ethane significantly. At a pressure of approximately 0.25 bar, the adsorption capacity of ethane is reduced from 1.9 mol/kg in the Na-SSZ-13 to 0.16 mol/kg in the Cu-SSZ-13. Based on the calculated Henry's constants for ethylene and ethane, Cu-SSZ-13 has an ideal adsorption selectivity of 490 while Na-SSZ-13 has an ideal adsorption selectivity of 44. This increases the adsorption selectivity by more than 11-fold with the inclusion of copper in the zeolite framework. This demonstrates that the presence of copper in the oxidation state of 2 significantly improves the separation capability of the SSZ-13 zeolite.

Example 3: Pure Component Equilibrium Adsorption on Copper-Exchanged SSZ-98

Equilibrium gas adsorption experiments for C2H4 and C2H6 were performed on a HPVA 200-4 4-port volumetric system. Samples were first activated at 300° C. to obtain the dry weight and then reactivated in the gas adsorption system. Gases used were C2H4, C2H6, and He (all 99.999%). The zeolites were tested from 0-10 bar for both C2H4 and C2H6. To demonstrate the capability of copper improving the adsorption affinity of ethylene over ethane, zeolites not ion-exchanged with copper were also tested under the same conditions.

Figure 3:
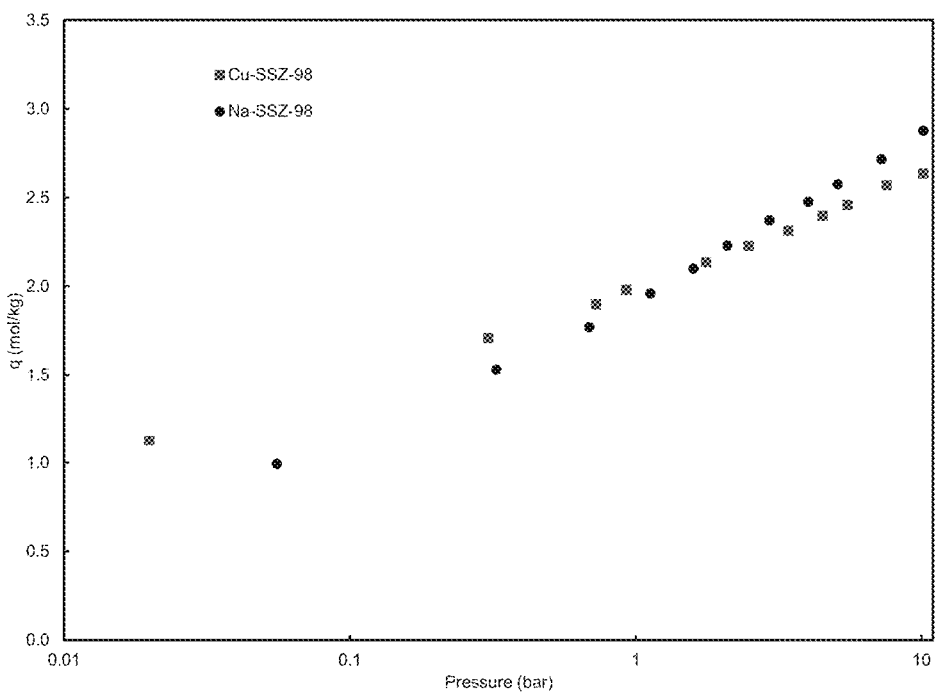
FIG. 3 is a plot of gas adsorption isotherms of C2H4 at 30 degrees C. for Cu-SSZ-98 and Na-SSZ-98.
Figure 4:
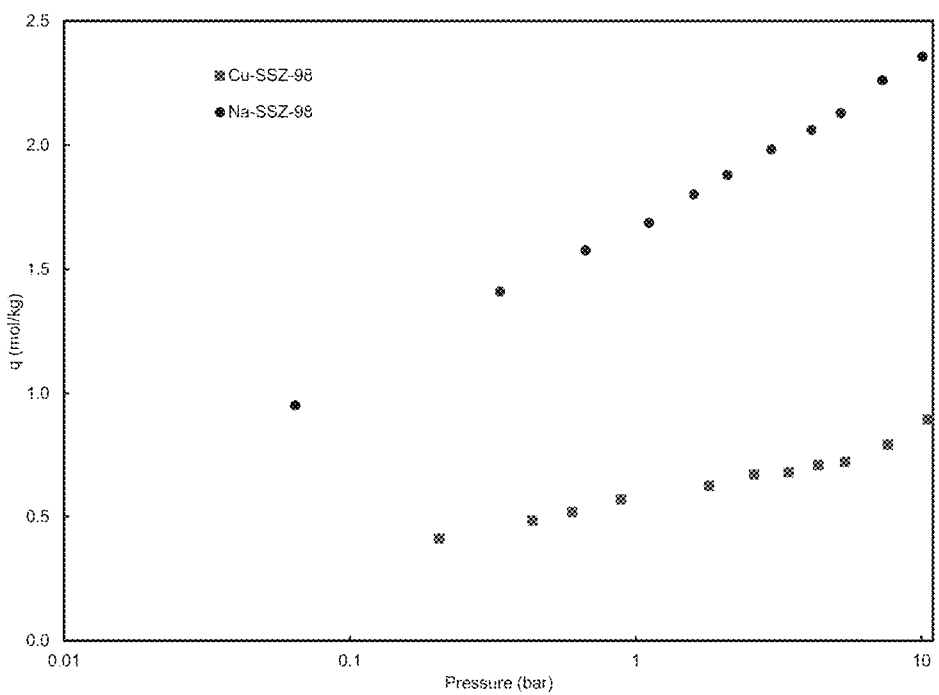
FIG. 4 is a plot of gas adsorption isotherms of C2H6 at 30 degrees C. for Cu-SSZ-98 and Na-SSZ-98.

FIG. 3 shows the equilibrium adsorption results for gas adsorption tests of ethylene for SSZ-98 zeolites samples containing either sodium or copper as the framework cation. FIG. 4 shows equilibrium adsorption results for gas adsorption tests of ethane for the SSZ-98 zeolite samples containing either sodium or copper as the framework cation. Comparison of ethylene isotherms in FIG. 3 demonstrates that SSZ-98 has an increase in affinity toward ethylene with the inclusion of copper in the framework. This is evidenced by an increase in the calculated Henry's constant for ethylene, increasing from 201 mol/kg/bar to 3700 mol/kg/bar. Comparison of ethane adsorption isotherms in FIG. 4 demonstrate a similar behavior observed for ion-exchanged SSZ-13 zeolites. With the inclusion of copper in the framework, there is a significantly decrease in the uptake and affinity toward ethane compared to the SSZ-98 sample containing sodium. Based on the calculated Henry's constants for ethylene and ethane, Cu-SSZ-98 has an ideal adsorption selectivity of 42 while Na-SSZ-98 has an ideal adsorption selectivity of 0.5. The adsorption selectivity increases by a factor of 84 when copper in the oxidation state of 2 is present in the zeolite SSZ-98 framework.

Example 4: Pure Component Equilibrium Adsorption on Copper-Exchanged ZSM-11

Equilibrium gas adsorption experiments for C2H4 and C2H6 were performed on a HPVA 200-4 4-port volumetric system. Samples were first activated at 300° C. to obtain the dry weight and then reactivated in the gas adsorption system. Gases used were C2H4, C2H6, and He (all 99.999%). The zeolites were tested from 0-10 bar for both C2H4 and C2H6. To demonstrate the capability of copper improving the adsorption affinity of ethylene over ethane, zeolites not ion-exchanged with copper were also tested under the same conditions.

Figure 5:
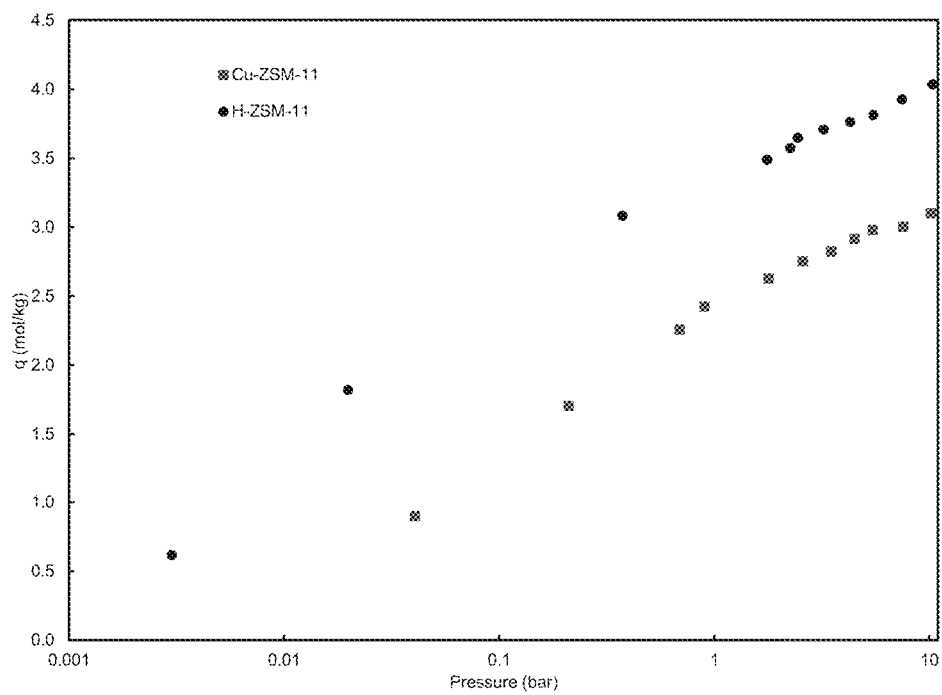
FIG. 5 is a plot of gas adsorption isotherms of C2H4 at 30 degrees C. for Cu-ZSM-11 and H-ZSM-11.
Figure 6:
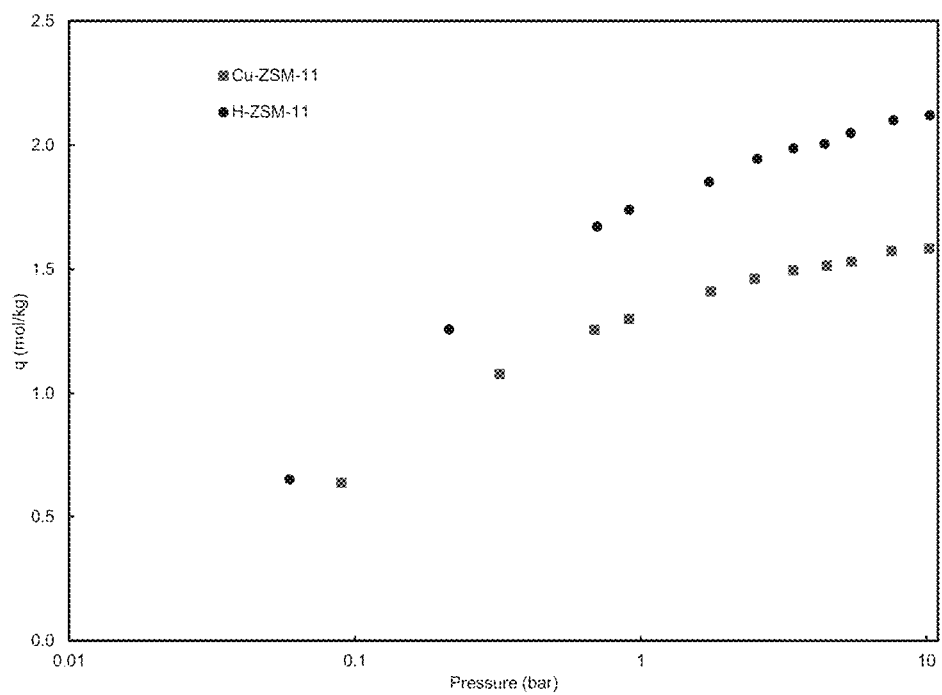
FIG. 6 is a plot of gas adsorption isotherms of C2H6 at 30 degrees C. for Cu-ZSM-11 and H-ZSM-11.

FIG. 5 shows the equilibrium adsorption results for gas adsorption tests of ethylene for ZSM-11 zeolites samples containing either proton or copper as the framework cation. FIG. 6 shows equilibrium adsorption results for gas adsorption tests of ethane for the ZSM-11 zeolite samples containing either proton or copper as the framework cation. Unlike the small-pore zeolites SSZ-13 and SSZ-98, the presence of copper in the ZSM-11 sample showed a decrease in the affinity toward ethylene in FIG. 5. Comparison of adsorption isotherms for ethane at 30 degrees C. in FIG. 6 demonstrate some degree of capacity reduction in Cu-ZSM-11 compared to H-ZSM-11, but the degree of reduction is not as great as it is in the small-pore zeolites SSZ-13 and SSZ-98. Therefore, the presence of copper (II) in zeolite frameworks appear to only benefit small-pore zeolites. The affinity toward ethylene is maintained or improved while also significantly reducing the available uptake of ethane in the zeolite framework for small-pore zeolites.

Example 5: Ethylene-Ethane Adsorption Selectivity

Figure 7:
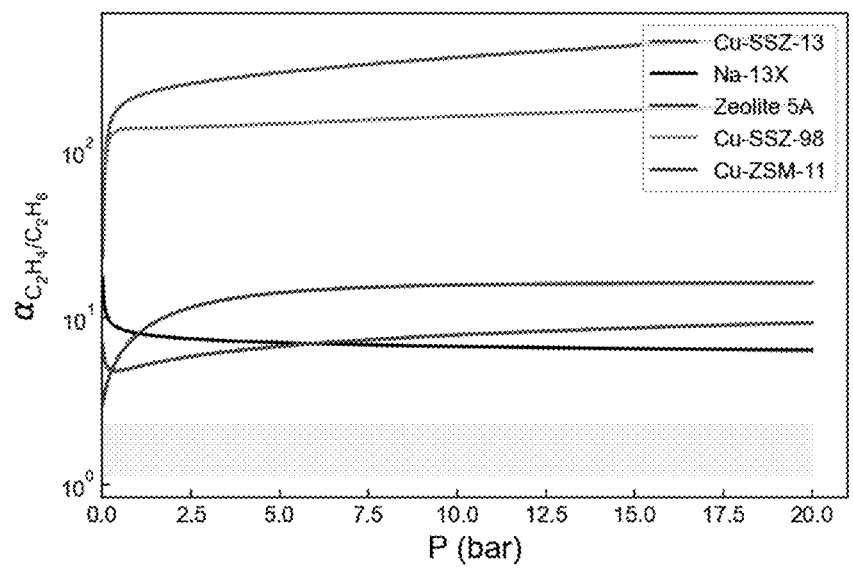
FIG. 7 is a plot of IAST adsorption selectivity with increasing system pressure for a 40%-60% ethane-ethylene gas at 30° C. Yellow bar indicates the distillation selectivity for this separation.

The adsorption isotherms in Examples 2-4 were used to estimate the adsorption mixture selectivity using Ideal Adsorbed Solution Theory (IAST). Literature data for Na-13X and zeolite 5A were used to compare against existing literature data for ethylene-selective adsorbents. A summary of the LAST modeling is shown in FIG. 7. As expected, due to the significantly lower ethane uptake in the copper-exchanged small-pore zeolites, the ethylene-ethane selectivity exceeds all the other adsorbents. Previously, zeolite 5A had shown the highest adsorption selectivity at 20 bar for small-pore zeolites. However, inclusion of copper cations in the small-pore zeolite frameworks improves the adsorption selectivity to 490 for SSZ-13 and 188 for SSZ-98. In both cases, these zeolites would be expected to achieve the desired 98% ethylene purity for an adsorption process.

Example 6: Pressure-Swing Adsorption Simulations

Figure 8:
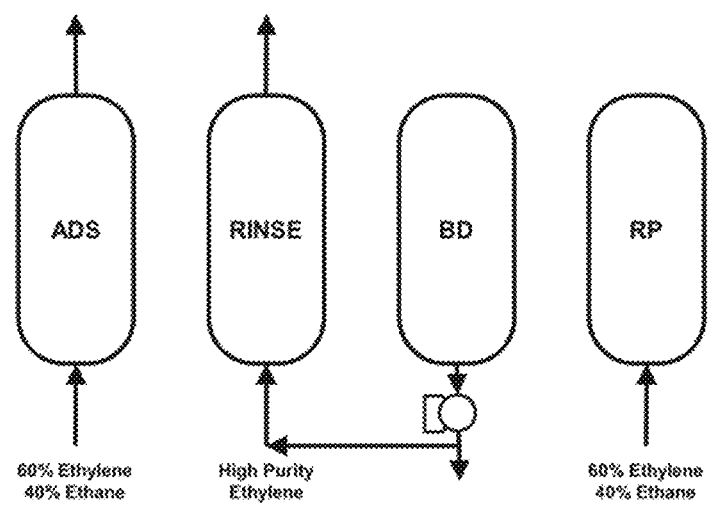
FIG. 8 is a diagram of the 4-step PSA cycle to recover adsorbed ethylene as high-purity product.

To evaluate the potential of using an equilibrium-selective adsorbent, pressure-swing adsorption simulations provide estimates for the process performance of an adsorbent material given a cycle configuration and cycle time for the separation to occur. Because such a high purity ethylene stream is desired as the product, a proposed PSA cycle which utilizes a rinse step of the high purity ethylene product is considered here as a first approach for recovery of ethylene. Shown in FIG. 8, the cycle has four basic steps: (1) feed of olefin-paraffin gas mixture; (2) rinse from the feed side using a compressed slipstream of the high purity olefin product; (3) blowdown and recovery of the adsorbed high purity olefin while also recycling a portion for the rinse step; and (4) repressurization of the bed using the feed gas mixture. An example of a PSA system to carry out such a PSA cycle is shown in FIG. 10. A more complex PSA cycle may be envisioned that has pressure equalization steps and a purge step that would help improve recovery of olefin further, but this 4-step cycle will give the minimum achievable product recovery for ethylene for a given adsorbent.

Example 7: Pressure-Swing Adsorption Experiments

To further evaluate the potential of using either an equilibrium-selective adsorbent, pressure-swing adsorption experiments provide estimates for the process performance of an adsorbent material given a cycle configuration and cycle time for the separation to occur. FIG. 10 shows an example of a 2-bed experimental PSA apparatus. Experiments were conducted on a 2-bed PSA test unit (PSA-1000) with customized control software provided by L&C Science and Technology (Hialeah, Fla.). The experimental PSA cycle operates similar to that shown in FIG. 8, but with two exceptions: (1) there is the added option of a pressure equalization step after the rinse and blowdown steps, and (2) there is no recycle stream between the blowdown and the rinse steps. In the experimental PSA rinse step, the user is free to specify the rinse gas, rinse gas flow rate and rinse duration independently. The stream leaving the outlet of the bed during the feed and rinse step is called the raffinate. During desorption or blowdown, the stream leaving the bed from the feed end is called the extract.

Two beds (1.66-cm diameter by 13.3-cm high) were each packed with approximately 20 grams of Cu-SSZ-13 extrudate. The PSA-1000 records the following data as functions of time: temperature and pressure of each bed, feed and rinse flowrates, and the raffinate rate and composition. The extract rate and composition are not measured directly, and thus needs to be calculated based on material balance over the entire PSA cycle. The compositions in the raffinate is measured by an online gas chromatograph (GC). An example PSA run is:

1. PSA run to operate for 10 cycles
2. Temperature maintained at 30° C.
3. Feed Pressurization with 50% ethylene/50% ethane at 437 sccm to 20 bar
4. Feed with 50% ethylene/50% ethane at 20 bar and 360 sccm for 7 min
5. Rinse with 100% ethylene at 20 bar and 108 sccm for 18 min
6. Pressure Equalization between beds 1 and 2
7. Blowdown to vacuum pressure (0.1 to 0.3 bar)
8. Pressure Equalization between beds 1 and 2

Figure 11:
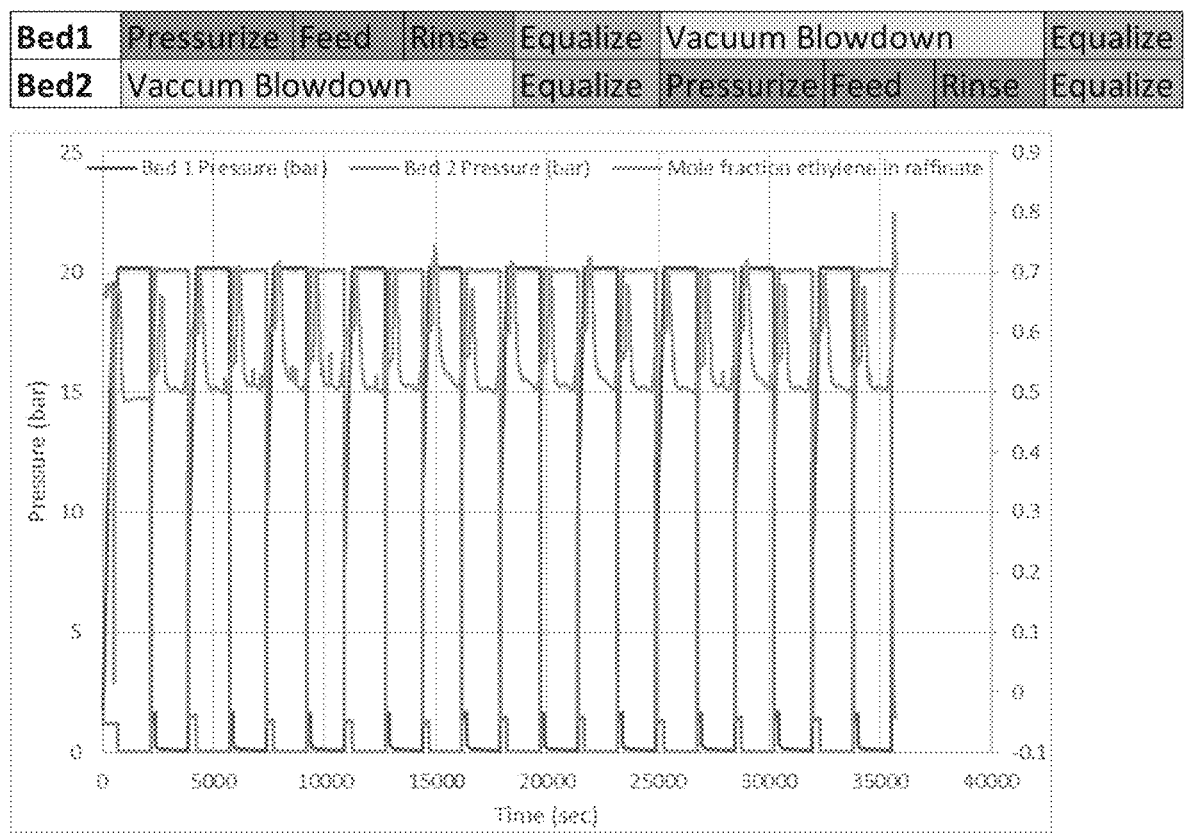
FIG. 11 is an example pressure profile and raffinate concentration from 2-bed PSA experiment.
Figure 12:
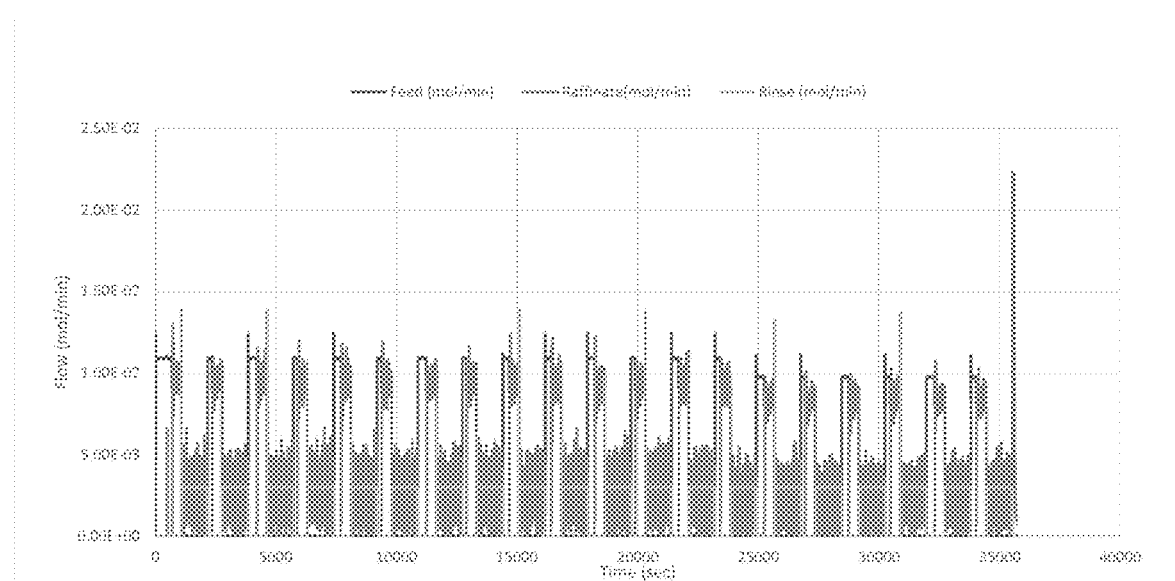
FIG. 12 is an example feed, rinse, and raffinate flow profiles during 2-bed PSA experiment.

FIG. 11 shows the pressure profiles of both beds and ethylene composition (mol %) in the raffinate during the PSA cycles, while FIG. 12 shows the flow data for feed, rinse, and raffinate. Note that each PSA bed operates the same cycle steps, but out of phase.

In order to determine the average ethylene purity and recovery, it is necessary to conduct a material balance through numerical integration of the curves in FIG. 12 along with the GC composition vs. time from FIG. 11. Table 1 shows an example calculation. The feed step includes the feed gas used during bed pressurization and adsorption. The raffinate stream is collected during process feed and rinse steps.

TABLE 1

Example material balance from PSA Experiment

| | Total Flow (mols) | Ethylene (mols) | Ethane (mols) |
|---|---|---|---|
| Total Feed | 1.99 | 0.98 | 1.01 |
| Rinse | 1.08 | 1.08 | 0.00 |
| Total Raffinate | 2.14 | 1.13 | 1.02 |
| Extract | 0.93 | 0.94 | −0.01 |
| Raffinate Rinse | 0.95 | 0.48 | 0.47 |
| Raffinate Feed | 1.19 | 0.64 | 0.55 |
| Estimated Ethylene Purity in Extract | | 101.25 | |

Within the margin of experimental error, close to 100% ethylene purity was produced in the extract rate.

In order to calculate the ethylene recovery, there are three definitions used in this work:

$$Rec1 = \frac{C2H4 \text{ in Extract}}{C2H4 \text{ in Feed} + \text{Rinse}}$$

$$Rec2 = 100 \frac{C2H4 \text{ in Extract} - C2H4 \text{ in Raffinate, Rinse}}{C2H4 \text{ in Feed} + \text{Rinse}}$$

$$Rec3 = 100 \frac{C2H4 \text{ in Extract} - \text{Rinse}}{C2H4 \text{ in Feed} + \text{Rinse}}$$

Rec 1 is defined as the gross recovery, which basically measures the total ethylene recovered in the blowdown step relative to the total ethylene fed into the process. From Table 1, Rec1=45.6%

Rec 2 is an estimated process recovery if the process would have included an internal recycle step where a portion of the blowdown stream is recompressed and used as the rinse step. The numerator factors in deduction of ethylene that is expected to be lost from the process in the bed exit during the rinse step. From Table 1, Rec2=22.5%.

Rec 3 is defined as the net recovery, which only tracks the total ethylene that was recovered from the original feed. From Table 1, Rec3=−6.9%. The negative number simply means the rinse rate is greater than the ethylene recovered in the extract during the PSA experiment. In reality, this situation is possible with a large internal recycle rate between the blowdown and rinse steps (refer to FIG. 8). Thus, Rec 2 may be a better predictor of overall process performance than either Rec 1 or Rec3 since it attempts to account for the portion of the ethylene that is expected to be lost during the rinse step in an actual process that utilizes a recycle step for the rinse.

The 2-bed PSA experiment disclosed here is consistent with the theoretical process modeling work of Example 6 and FIG. 9. Equilibrium-selective adsorbents such as Cu-SSZ-13 can produce>98% ethylene purity using a PSA cycle with an appropriate rinse step and choice of cycle conditions.

The invention claimed is:

1. A method for removing impurities from a feed gas stream of ethylene-containing stranded gas including ethylene and impurities comprising nitrogen, hydrogen, and/or ethane, comprising:
   a. alternating an input of the feed gas stream between at least two beds of one or more adsorbent particles made from a homogeneous mixture, wherein the one or more adsorbent particles comprise a zeolite SSZ-13;
   b. wherein the feed gas stream contacts one of the at least two beds at a given time by an adsorption step and a product gas stream is simultaneously vented from another of the at least two beds by a desorption step;
   c. wherein the contacting of the one of the at least two beds by the feed gas stream occurs at a feed pressure of from about 50 psia to about 500 psia for a sufficient time to preferentially adsorb the ethylene from the feed gas stream and thereby produces the product gas stream during the desorption step containing no greater than about 2 mol % impurities and at least about 98 mol % of the ethylene recovered from the feed gas stream; and
   d. wherein the feed gas stream is input at a feed end of each of the at least two beds, and an impurity-enriched gas stream is produced after adsorption of the ethylene and removed at the feed end, and wherein the product gas stream is removed at a product end of each of the at least two beds.

2. The method of claim 1, wherein the zeolite SSZ-13 has a Si:Al mole ratio of 5 to 100 in the framework.

3. The method of claim 1, wherein the zeolite SSZ-13 has sodium as a framework cation.

4. The method of claim 1, wherein the zeolite SSZ-13 has copper(II) as a framework cation.

5. The method of claim 1, wherein the method utilizes two beds of the one or more adsorbent particles, and further comprising:
   a. following the adsorption step in one of the two beds and a simultaneous desorption step in the other of the two beds, compressing a slip-stream of the product gas from the desorption step, using the compressed slip-stream as a rinse stream to rinse the one of the two beds after the adsorption step, equalizing a pressure of the one of the two beds and the other of the two beds through the feed end of each of the one of the two beds and the other of the two beds at an end of the rinse and the simultaneous desorption step; and b. re-pressurizing the other of the two beds having just completed the simultaneous desorption step and pressure equalization step by sending the feed gas through the feed end of the other bed while closing the product end of the other bed.

6. The method of claim 1, wherein the method utilizes two beds of the one or more adsorbent particles, and further comprising:

a. following the adsorption step in one of the two beds and a simultaneous desorption step in the other of the two beds, compressing a slip-stream of the product gas from the desorption step, using the compressed slip-stream as a rinse stream to rinse the one of the two beds after the adsorption step, equalizing a pressure of the one of the two beds and the other of the two beds through the product end of each of the one of the two beds and the other of the two beds at an end of the rinse step and the simultaneous desorption step; and b. re-pressurizing the other of the two beds having just completed the simultaneous desorption step and pressure equalization step by sending the feed gas through the feed end of the other bed while closing the product end of the other bed.

7. A method for removing impurities from a feed gas stream of ethylene-containing stranded gas including ethylene and impurities comprising nitrogen, hydrogen, and/or ethane, comprising:

a. alternating an input of the feed gas stream between at least two beds of one or more adsorbent particles made from a homogeneous mixture, wherein the one or more adsorbent particles comprise a zeolite SSZ-98;

b. wherein the feed gas stream contacts one of the at least two beds at a given time by an adsorption step and a product gas stream is simultaneously vented from another of the at least two beds by a desorption step;

c. wherein the contacting of the one of the at least two beds by the feed gas stream occurs at a feed pressure of from about 50 psia to about 500 psia for a sufficient time to preferentially adsorb the ethylene from the feed gas stream and thereby produces the product gas stream during the desorption step containing no greater than about 2 mol % impurities and at least about 98 mol % of the ethylene recovered from the feed gas stream; and d. wherein the feed gas stream is input at a feed end of each of the at least two beds, and an impurity-enriched gas stream is produced after adsorption of the ethylene and removed at the feed end, and wherein the product gas stream is removed at a product end of each of the at least two beds.

8. The method of claim 7, wherein the zeolite SSZ-98 has a Si:Al mole ratio of 5 to 100 in the framework.

9. The method of claim 7, wherein the zeolite SSZ-98 has sodium as a framework cation.

10. The method of claim 7, wherein the zeolite SSZ-98 has copper(II) as a framework cation.

11. The method of claim 7, wherein the method utilizes two beds of the one or more adsorbent particles, and further comprising:

a. following the adsorption step in one of the two beds and a simultaneous desorption step in the other of the two beds, compressing a slip-stream of the product gas from the desorption step, using the compressed slip-stream as a rinse stream to rinse the one of the two beds after the adsorption step, equalizing a pressure of the one of the two beds and the other of the two beds through the feed end of each of the one of the two beds and the other of the two beds at an end of the rinse and the simultaneous desorption step; and b. re-pressurizing the other of the two beds having just completed the simultaneous desorption and pressure equalization step by sending the feed gas through the feed end of the other bed while closing the product end of the other bed.

12. The method of claim 7, wherein the method utilizes two beds of the one or more adsorbent particles, and further comprising:

a. following the adsorption step in one of the two beds and a simultaneous desorption step in the other of the two beds, compressing a slip-stream of the product gas from the desorption step, using the compressed slip-stream as a rinse stream to rinse the one of the two beds after the adsorption step, equalizing a pressure of the one of the two beds and the other of the two beds through the product end of each of the one of the two beds and the other of the two beds at an end of the rinse step and the simultaneous desorption step; and b. re-pressurizing the other of the two beds having just completed the simultaneous desorption step and pressure equalization step by sending the feed gas through the feed end of the other bed while closing the product end of the other bed.

\* \* \* \* \*